(12) United States Patent
Schuele et al.

(10) Patent No.: US 10,022,270 B2
(45) Date of Patent: Jul. 17, 2018

(54) LASER CAPSULOVITREOTOMY

(71) Applicant: OptiMedica Corporation, Santa Ana, CA (US)

(72) Inventors: Georg Schuele, Portola Valley, CA (US); Julian Stevens, Sunnyvale, CA (US); Dan E. Andersen, Menlo Park, CA (US)

(73) Assignee: OPTIMEDICA CORPORATION, Santa Ana, CA (US)

( * ) Notice: Subject to any disclaimer, the term of this patent is extended or adjusted under 35 U.S.C. 154(b) by 443 days.

(21) Appl. No.: 14/190,915

(22) Filed: Feb. 26, 2014

(65) Prior Publication Data

US 2014/0276676 A1    Sep. 18, 2014

Related U.S. Application Data

(60) Provisional application No. 61/785,672, filed on Mar. 14, 2013.

(51) Int. Cl.
*A61F 9/008* (2006.01)

(52) U.S. Cl.
CPC .......... *A61F 9/00834* (2013.01); *A61F 9/008* (2013.01); *A61F 9/00836* (2013.01);
(Continued)

(58) Field of Classification Search
None
See application file for complete search history.

(56) References Cited

U.S. PATENT DOCUMENTS

| | | | |
|---|---|---|---|
| 4,174,389 A * | 11/1979 | Cope | A61K 38/4886 424/94.67 |
| 4,309,998 A * | 1/1982 | Aron nee Rosa | A61B 18/201 372/26 |

(Continued)

FOREIGN PATENT DOCUMENTS

| | | | |
|---|---|---|---|
| WO | 2009039302 A2 | 3/2009 | |
| WO | WO 2011151064 A1 * | 12/2011 | ............ A61F 9/008 |
| WO | 2012158183 A1 | 11/2012 | |

OTHER PUBLICATIONS

Ascaso et al., Neodymium: Yttrium-Aluminum-Garnet Laser Anterior Hyaloidotomy to Treat Trapped Triamcinolone Acetonide Behind the Crystalline Lens After Intravitreal Injection, Middle East Afr J Ophthalmol. Jan.-Mar. 2012; 19(1): 163-165.*

(Continued)

*Primary Examiner* — Lynsey Eiseman
*Assistant Examiner* — Manolis Pahakis
(74) *Attorney, Agent, or Firm* — Johnson & Johnson Surgical Vision, Inc.

(57) ABSTRACT

Methods and systems for performing laser-assisted surgery on an eye form a layer of bubbles in the Berger's space of the eye to increase separation between the posterior portion of the lens capsule of the eye and the anterior hyaloid surface of the eye. A laser is used to form the layer of bubbles in the Berger's space. The increased separation between the posterior portion of the lens capsule and the anterior hyaloid surface can be used to facilitate subsequent incision of the posterior portion of the lens capsule with decreased risk of compromising the anterior hyaloid surface. For example, the layer of bubbles can be formed prior to performing a capsulotomy on the posterior portion of the lens capsule.

2 Claims, 4 Drawing Sheets

(52) U.S. Cl.
CPC .............. *A61F 2009/0087* (2013.01); *A61F 2009/00889* (2013.01)

(56) References Cited

U.S. PATENT DOCUMENTS

| | | | |
|---|---|---|---|
| 4,560,383 A * | 12/1985 | Leiske | A61F 2/16 623/6.51 |
| 5,459,570 A | 10/1995 | Swanson et al. | |
| 5,720,894 A | 2/1998 | Neev et al. | |
| 5,748,352 A | 5/1998 | Hattori | |
| 5,748,898 A | 5/1998 | Ueda | |
| 5,957,915 A | 9/1999 | Trost | |
| 5,984,916 A | 11/1999 | Lai | |
| 6,019,472 A | 2/2000 | Koester et al. | |
| 6,027,531 A * | 2/2000 | Tassignon | A61F 2/16 623/6.4 |
| 6,053,613 A | 4/2000 | Wei et al. | |
| 6,111,645 A | 8/2000 | Tearney et al. | |
| 6,454,761 B1 | 9/2002 | Freedman | |
| 6,881,225 B2 | 4/2005 | Okada | |
| 7,655,002 B2 | 2/2010 | Myers et al. | |
| 7,717,907 B2 | 5/2010 | Ruiz et al. | |
| 8,262,646 B2 | 9/2012 | Frey et al. | |
| 8,350,183 B2 | 1/2013 | Vogel et al. | |
| 8,382,745 B2 | 2/2013 | Naranjo-Tackman et al. | |
| 8,414,564 B2 | 4/2013 | Goldshleger et al. | |
| 9,849,032 B2 * | 12/2017 | Schuele | A61F 9/00804 |
| 9,849,033 B2 * | 12/2017 | Schuele | A61F 9/00804 |
| 2002/0091321 A1 * | 7/2002 | Goldstein | A61B 5/0059 600/476 |
| 2003/0187501 A1 * | 10/2003 | Okada | A61F 2/1613 623/6.4 |
| 2005/0107773 A1 * | 5/2005 | Bergt | B23K 26/08 606/4 |
| 2005/0165387 A1 * | 7/2005 | Lubatschowski | A61F 9/008 606/5 |
| 2008/0281413 A1 * | 11/2008 | Culbertson | A61F 2/16 623/6.12 |
| 2009/0149841 A1 * | 6/2009 | Kurtz | A61B 18/20 606/4 |
| 2010/0022996 A1 | 1/2010 | Frey et al. | |
| 2010/0191226 A1 * | 7/2010 | Blumenkranz | A61F 9/00736 606/4 |
| 2010/0324543 A1 * | 12/2010 | Kurtz | A61F 9/008 606/6 |
| 2011/0118713 A1 * | 5/2011 | Raksi | A61F 9/00825 606/6 |
| 2011/0184395 A1 * | 7/2011 | Schuele | A61F 9/008 606/5 |
| 2011/0196350 A1 * | 8/2011 | Friedman | A61F 9/008 606/6 |
| 2011/0202046 A1 * | 8/2011 | Angeley | G06T 7/149 606/6 |
| 2011/0245814 A1 * | 10/2011 | Taboada | A61F 9/008 606/4 |
| 2011/0319873 A1 | 12/2011 | Raksi et al. | |
| 2011/0319875 A1 | 12/2011 | Loesel et al. | |
| 2012/0089134 A1 * | 4/2012 | Horvath | A61F 9/00825 606/6 |
| 2012/0296319 A1 | 11/2012 | Chaudhary et al. | |
| 2013/0131652 A1 * | 5/2013 | Dick | A61F 9/008 606/4 |
| 2014/0039048 A1 * | 2/2014 | Bavik | A61K 31/138 514/459 |
| 2014/0074074 A1 * | 3/2014 | Dick | A61F 9/00825 606/6 |
| 2014/0316389 A1 * | 10/2014 | Schuele | A61F 9/00804 606/5 |
| 2015/0148786 A1 * | 5/2015 | Plunkett | A61F 9/008 606/4 |
| 2015/0216730 A1 * | 8/2015 | Schuele | A61F 9/00834 606/6 |

OTHER PUBLICATIONS

Aaberg et al., Management of anterior and posterior proliferative vitreoretinopathy. XLV. Edward Jackson memorial lecture, Am J Ophthalmol. Nov. 15, 1988;106(5):519-32, abstract only.*
Melamed et al., Nd-YAG laser hyaloidotomy for malignant glaucoma following one-piece 7 mm intraocular lens implantation, BritishJournal ofOphthalmology, 1991,75,501-503.*
Ozyol et al., The role of anterior hyaloid face integrity on retinal complications during Nd: YAG laser capsulotomy, Graefes Arch Clin Exp Ophthalmol (2014) 252:71-75.*
Kramer et al, Capsulovutreotomy: A technique for intracapsular lens extraction in cats, Investigative Ophthalmology, May 1971.*
International Search Report and Written Opinion for Application No. PCT/US2014/018710, dated May 12, 2014, 10 pages.
Co-pending U.S. Appl. No. 11/328,970, filed Jan. 9, 2006.

* cited by examiner

LASER CAPSULOVITREOTOMY

CROSS-REFERENCES TO RELATED APPLICATIONS

This application claims priority to U.S. provisional application No. 61/785,672 filed on Mar. 14, 2013, the entire contents of which are incorporated herein by reference.

BACKGROUND

Cataract extraction is one of the most commonly performed surgical procedures in the world. A cataract is formed by opacification of the crystalline lens or its envelope—the lens capsule—of the eye. The cataract obstructs passage of light through the lens. A cataract can vary in degree from slight to complete opacity. Early in the development of an age-related cataract the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. Cataracts are potentially blinding if untreated.

A common cataract treatment involves replacing the opaque crystalline lens with an artificial intraocular lens (IOL). Presently, an estimated 15 million cataract surgeries per year are performed worldwide. The cataract treatment market is composed of various segments including intraocular lenses for implantation, viscoelastic polymers to facilitate surgical maneuvers, and disposable instrumentation including ultrasonic phacoemulsification tips, tubing, various knives, and forceps.

Presently, cataract surgery is typically performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small round hole is formed in the anterior side of the lens capsule. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye through a small incision. Typically, the IOL is held in place by the edges of the anterior capsule and the capsular bag. The IOL may also be held by the posterior capsule, either alone or in unison with the anterior capsule. This latter configuration is known in the field as a "Bag-in-Lens" implant.

One of the most technically challenging and critical steps in the cataract extraction procedure is providing access to the lens nucleus. The manual continuous curvilinear capsulorhexis (CCC) procedure evolved from an earlier technique termed can-opener capsulotomy in which a sharp needle was used to perforate the anterior lens capsule in a circular fashion followed by the removal of a circular fragment of lens capsule typically in the range of 5-8 mm in diameter. The smaller the capsulotomy, the more difficult it is to produce manually. The capsulotomy facilitates the next step of nuclear sculpting by phacoemulsification. Due to a variety of complications associated with the initial can-opener technique, attempts were made by leading experts in the field to develop a better technique for removal of the anterior lens capsule preceding the emulsification step.

The desired outcome of the manual continuous curvilinear capsulorhexis is to provide a smooth continuous circular opening through which not only the phacoemulsification of the nucleus can be performed safely and easily, but also to provide for easy insertion of the intraocular lens. The resulting opening in the anterior capsule provides both a clear central access for tool insertion during removal of the nucleus and for IOL insertion, a permanent aperture for transmission of the image to the retina of the patient, and also support of the IOL inside the remaining capsule that limits the potential for dislocation.

Furthermore, IOLs that engage the posterior capsule can benefit from a posterior capsulotomy. An example of such an IOL that can benefit from a posterior capsulotomy is described in U.S. Pat. Appl. No. 2008/0281413, entitled "METHOD AND APPARATUS FOR CREATING INCISIONS TO IMPROVE INTRAOCULAR LENS PLACEMENT", in the name of Culbertson, et al., the entire disclosure of which is incorporated herein by reference. Such lenses may further benefit from seating the IOL in both the anterior and posterior capsule in order to best provide for accommodative motion via the zonular process. Creating a posterior capsulotomy, however, may require the surgeon to engage the vitreous and its anterior hyaloid surface. Unfortunately, the anterior hyaloid surface may be violated during the posterior capsulotomy procedure. It is postulated that a broken anterior hyaloid surface may allow anterior movement of proteins and macromolecules from the vitreous gel, which may result in fluid shifting within an already syneretic vitreous cavity. This anterior movement of proteins and macromolecules may lead to increased peripheral retinal traction and break formation. Even with an intact anterior hyaloid surface, a rent in the posterior capsule disrupts the physical barrier between the anterior and posterior segments of the eye similar to that of the aphakic eye after intracapsular lens extraction. The loss of this barrier may facilitate diffusion of hyaluronic acid, a stabilizer of the vitreous gel, into the anterior chamber; this situation may manifest clinically as collapse of the vitreous gel.

Accordingly, improved methods, techniques, and an apparatus are needed to perform an accurate posterior capsulotomy with reduced risk of compromising the anterior hyaloid surface.

SUMMARY

Although specific reference is made to the removal and treatment of a cataract, the methods and apparatus as described herein can be used with one or more of many surgical procedures, for example a posterior capsulotomy on a non-cataractous eye of a patient.

Embodiments provide methods and systems for performing laser-assisted surgery on an eye to provide a separation layer between the posterior portion of the lens capsule of the eye and the anterior hyaloid surface of the eye. While the separation layer can be formed in one or more of many ways, in many embodiments a layer of bubbles is formed in the Berger's space of the eye to separate the posterior portion of the lens capsule of the eye and the anterior hyaloid surface of the eye. The increased separation between the posterior portion of the lens capsule and the anterior hyaloid surface reduces the risk of compromising the anterior hyaloid surface during a subsequent procedure in which the posterior portion of the lens capsule is incised. In many embodiments, the layer of bubbles is formed prior to performing a capsulotomy on the posterior portion of the lens capsule. The capsulotomy can be performed in combination with one or more of many surgical procedures, such as the implantation of an IOL which may comprise an accommodating IOL or a non-accommodating IOL.

Thus, in one aspect, a method is provided for performing laser-assisted surgery on an eye having a lens capsule, an anterior hyaloid surface, and a Berger's space between a posterior portion of the lens capsule and the anterior hyaloid surface. The method includes using a laser to form bubbles within the Berger's space to increase separation between the posterior portion of the lens capsule and the anterior hyaloid surface. After forming the bubbles, the posterior portion of the lens capsule in incised. In many embodiments, the laser is used to perform the incising of the posterior portion of the lens capsule. And in many embodiments, the laser is used to perform a capsulotomy on the posterior portion of the lens capsule.

In another aspect, a system is provided for performing laser-assisted surgery on an eye having a lens capsule, an anterior hyaloid surface, and a Berger's space between a posterior portion of the lens capsule and the anterior hyaloid surface. The system includes a laser source, an integrated optical system, and a controller. The laser source is configured to produce a treatment beam including a plurality of laser pulses. The integrated optical system includes an imaging assembly operatively coupled to a treatment laser delivery assembly such that they share at least one common optical element. The integrated optical system is configured to acquire image information pertinent to one or more targeted tissue structures and direct the treatment beam in a three-dimensional pattern to cause breakdown in at least one of the targeted tissue structures. The controller is operatively coupled with the laser source and the integrated optical system. The controller is configured to control the system to form a plurality of bubbles within the Berger's space to increase separation between the posterior portion of the lens capsule and the anterior hyaloid surface. In many embodiments, the controller is configured to control the system to incise the posterior portion of the lens capsule subsequent to the formation of the plurality of bubbles within the Berger's space. And in many embodiments, the controller is configured to control the system to perform a capsulotomy on the posterior portion of the lens capsule subsequent to the formation of the plurality of bubbles within the Berger's space.

For a fuller understanding of the nature and advantages of the present disclosure, reference should be made to the ensuing detailed description and accompanying drawings. Other aspects, objects and advantages of the disclosure will be apparent from the drawings and detailed description that follows.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which.

DETAILED DESCRIPTION

In the following description, various embodiments of the present disclosure will be described. For purposes of explanation, specific configurations and details are set forth in order to provide a thorough understanding of the embodiments. However, it will also be apparent to one skilled in the art that the present disclosure may be practiced without the specific details. Furthermore, well-known features may be omitted or simplified in order not to obscure the embodiment being described.

Methods and systems for performing laser-assisted surgery on an eye use a laser form a layer of bubbles in the Berger's space of the eye. The layer of bubbles serves to increase separation between the posterior portion of the lens capsule of the eye and the anterior hyaloid surface of the eye. The increased separation between the posterior portion of the lens capsule and the anterior hyaloid surface can be used to decrease risk of compromising the anterior hyaloid surface during a subsequent incision of the posterior portion of the lens capsule. For example, the layer of bubbles can be formed prior to performing a capsulotomy on the posterior portion of the lens capsule.

Figure 1:
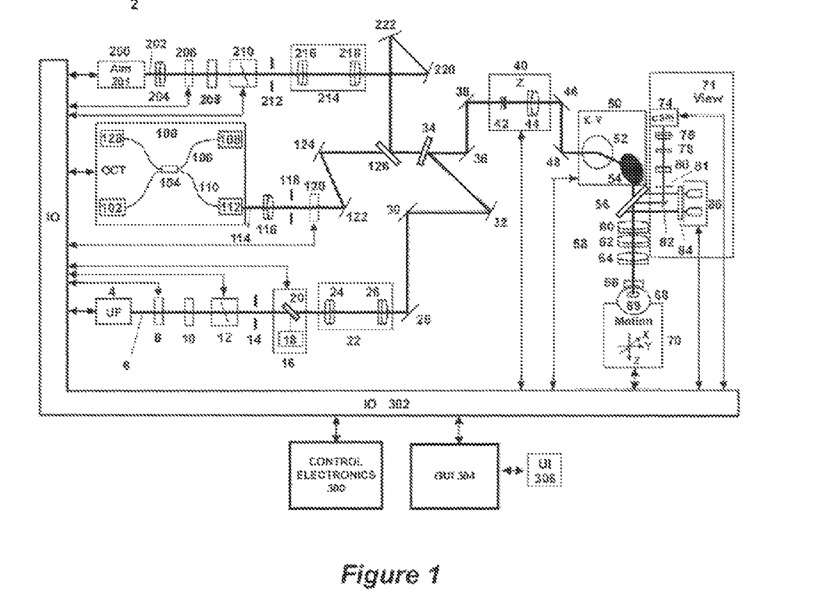
FIG. 1 shows a schematic representation of an embodiment of a system capable of creating bubbles within the anterior hyaloid vitreous of Berger's space, in accordance with many embodiments.

The methods disclosed herein can be implemented by a system that projects or scans an optical beam into a patient's eye 68, such as system 2 shown in FIG. 1. System 2 includes an ultrafast (UF) light source 4 (e.g., a femtosecond laser). Using system 2, a beam can be scanned in the patient's eye 68 in three dimensions: X, Y, Z. Short-pulsed laser light can be focused into eye tissue to produce dielectric breakdown to cause photo disruption around the focal point (the focal zone), thereby rupturing the tissue in the vicinity of the photo-induced plasma. In this embodiment, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. And threshold energy, time to complete the procedure, and stability bound the lower limit for pulse energy and repetition rate. The peak power of the focused spot in the eye 68 and specifically within the crystalline lens 69 and anterior capsule of the eye is sufficient to produce optical breakdown and initiate a plasma-mediated ablation process. Near-infrared wavelengths are preferred because linear optical absorption and scattering in biological tissue is reduced for near-infrared wavelengths. As a non-limiting example, laser 4 can be a repetitively pulsed 1035 nm device that produces 500 fs pulses at a repetition rate of 100 kHz and individual pulse energy in the 1 to 20 micro joule range.

Alternately, a system of longer pulse duration and higher energy can be used to create larger bubbles for enhanced efficiency. Using a supine patient, the resulting bubbles will float upwards. This reduces the accuracy requirement of the targeting system. In general, any suitable laser having any suitable parameters can be used.

The laser 4 is controlled by control electronics 300, via an input and output device 302, to create optical beam 6. Control electronics 300 may comprise a processor such as a computer, microcontroller, etc. In this example, the controller 300 controls the entire system and data is moved through input/output device IO 302. A graphical user interface GUI 304 can be used to set system operating parameters, process user input (UI) 306, and display gathered information such as images of ocular structures. The GUI 304 and UI 306 may comprise components of a known computer system, for example one or more of a display, a touch screen display, key board, a pointer or a mouse, for example. The control electronics may comprise one or more processors of a computer system, for example.

The control electronics 300 can be configured in one or more of many ways, and may comprise a processor having a tangible medium having instructions of a computer program embodied thereon. In many embodiments, the tangible medium comprises a computer readable memory having instructions of a computer readable medium embodied thereon. Alternatively or in combination, the control electronic may comprise array logic such as a gate array, a programmable gate array, for field programmable gate array to implement one or more instructions as described herein. The instructions of the tangible medium can be implemented by the processor of the control electronics.

The generated UF light beam 6 proceeds towards the patient eye 68 passing through a half-wave plate 8 and a linear polarizer, 10. The polarization state of the beam can be adjusted so that the desired amount of light passes through the half-wave plate 8 and the linear polarizer 10, which together act as a variable attenuator for the UF beam 6. Additionally, the orientation of the linear polarizer 10 determines the incident polarization state incident upon a beam combiner 34, thereby optimizing the beam combiner 34 throughput.

The UF light beam 6 proceeds through a system-controlled shutter 12, an aperture 14, and a pickoff device 16. The system-controlled shutter 12 ensures on/off control of the laser for procedural and safety reasons. The aperture 14 sets an outer useful diameter for the UF light beam 6 and the pickoff device 16 monitors the resulting beam. The pickoff device 16 includes a partially reflecting mirror 20 and a detector 18. Pulse energy, average power, or a combination can be measured using the detector 18. Output from the detector 18 can be used for feedback to the half-wave plate 8 for attenuation and to verify whether the system-controlled shutter 12 is open or closed. In addition, the system-controlled shutter 12 can have position sensors to provide a redundant state detection.

The beam passes through a beam conditioning stage 22, in which beam parameters such as beam diameter, divergence, circularity, and astigmatism can be modified. In this illustrative example, the beam conditioning stage 22 includes a two-element beam expanding telescope comprised of spherical optics 24, 26 in order to achieve the intended beam size and collimation. Although not illustrated here, an anamorphic or other optical system can be used to achieve the desired beam parameters. The factors used to determine these beam parameters include the output beam parameters of the laser, the overall magnification of the system, and the desired numerical aperture (NA) at the treatment location. In addition, the beam conditioning stage 22 can be used to image aperture 14 to a desired location (e.g., the center location between a 2-axis scanning device 50 described below). In this way, the amount of light that makes it through the aperture 14 is assured to make it through the scanning system. The pickoff device 16 is then a reliable measure of the usable light.

After exiting the beam conditioning stage 22, the beam 6 reflects off of fold mirrors 28, 30, 32. These mirrors can be adjustable for alignment purposes. The beam 6 is then incident upon the beam combiner 34. The beam combiner 34 reflects the UF beam 6 (and transmits both the imaging, in this exemplary case, an optical coherence tomography (OCT) beam 114, and an aim 202 beam described below). For efficient beam combiner operation, the angle of incidence is preferably kept below 45 degrees and the polarization of the beams is fixed where possible. For the UF beam 6, the orientation of the linear polarizer 10 provides fixed polarization. Although OCT is used as the imaging modality in this non-limiting example, other approaches, such as Purkinje imaging, Scheimpflug imaging, confocal or non-linear optical microscopy, fluorescence imaging, ultrasound, structured light, stereo imaging, or other known ophthalmic or medical imaging modalities and/or combinations thereof may be employed.

Following the beam combiner 34, the beam 6 continues onto a z-adjust or Z scan device 40. In this illustrative example the z-adjust 40 includes a Galilean telescope with two lens groups 42, 44 (each lens group includes one or more lenses). The lens group 42 moves along the z-axis about the collimation position of the telescope. In this way, the focus position of the spot in the patient's eye 68 moves along the z-axis as indicated. In general, there is a fixed linear relationship between the motion of lens 42 and the motion of the focus. In this case, the z-adjust telescope has an approximate 2× beam expansion ratio and a 1:1 relationship of the movement of lens 42 to the movement of the focus. Alternatively, the lens group 44 could be moved along the z-axis to actuate the z-adjust, and scan. The z-adjust 40 is the z-scan device for treatment in the eye 68. It can be controlled automatically and dynamically by the system and selected to be independent or to interplay with the X-Y scan device described next. The mirrors 36, 38 can be used for aligning the optical axis with the axis of the z-adjust device 40.

After passing through the z-adjust device 40, the beam 6 is directed to the x-y scan device 50 by mirrors 46, 48. The mirrors 46, 48 can be adjustable for alignment purposes. X-Y scanning is achieved by the scanning device 50 preferably using two mirrors 52, 54 under the control of the control electronics 300, which rotate in orthogonal directions using motors, galvanometers, or any other well known optic moving device. The mirrors 52, 54 are located near the telecentric position of an objective lens 58 and a contact lens 66 combination described below. Tilting the mirrors 52, 54 changes the resulting direction of the beam 6, causing lateral displacements in the plane of UF focus located in the patient's eye 68. The objective lens 58 may be a complex multi-element lens element, as shown, and represented by lenses 60, 62, and 64. The complexity of the objective lens 58 will be dictated by the scan field size, the focused spot size, the available working distance on both the proximal and distal sides of objective lens 58, as well as the amount of aberration control. An f-theta objective lens 58 of focal length 60 mm generating a spot size of 10 μm, over a field of 10 mm, with an input beam size of 15 mm diameter is an example. Alternatively, X-Y scanning by the scanning device 50 may be achieved by using one or more moveable optical elements (e.g., lenses, gratings), which also may be controlled by the control electronics 300, via the input and output device 302.

The scanning device 50 under the control of the control electronics 300 can automatically generate the aiming and treatment scan patterns. Such patterns may be comprised of a single spot of light, multiple spots of light, a continuous pattern of light, multiple continuous patterns of light, and/or any combination of these. In addition, the aiming pattern (using the aim beam 202 described below) need not be identical to the treatment pattern (using the light beam 6), but preferably at least defines its boundaries in order to assure that the treatment light is delivered only within the desired target area for patient safety. This may be done, for example, by having the aiming pattern provide an outline of the intended treatment pattern. This way the spatial extent of the treatment pattern may be made known to the user, if not the exact locations of the individual spots themselves, and the scanning thus optimized for speed, efficiency and accuracy. The aiming pattern may also be made to be perceived as blinking in order to further enhance its visibility to the user.

An optional contact lens 66, which can be any suitable ophthalmic lens, can be used to help further focus the light beam 6 into the patient's eye 68 while helping to stabilize eye position. The positioning and character of the light beam 6 and/or the scan pattern the light beam 6 forms on the eye 68 may be further controlled by use of an input device such as a joystick, or any other appropriate user input device (e.g., GUI 304) to position the patient and/or the optical system.

The UF laser 4 and the control electronics 300 can be set to target the targeted structures in the eye 68 and ensure that the light beam 6 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished using one or more methods including direct observation of an aiming beam, or other known ophthalmic or medical imaging modalities, such as those mentioned above, and/or combinations thereof. In the embodiment of FIG. 1, an OCT device 100 is described, although other modalities are within the scope of the present disclosure. An OCT scan of the eye will provide information about the axial location of the anterior and posterior lens capsule, the boundaries of the cataract nucleus, as well as the depth of the anterior chamber. This information is then loaded into the control electronics 300, and used to program and control the subsequent laser-assisted surgical procedure. The information may also be used to determine a wide variety of parameters related to the procedure such as, for example, the upper and lower axial limits of the focal planes used for cutting the lens capsule and segmentation of the lens cortex and nucleus, and the thickness of the lens capsule among others.

The OCT device 100 in FIG. 1 includes a broadband or a swept light source 102 that is split by a fiber coupler 104 into a reference arm 106 and a sample arm 110. The reference arm 106 includes a module 108 containing a reference reflection along with suitable dispersion and path length compensation. The sample arm 110 of the OCT device 100 has an output connector 112 that serves as an interface to the rest of the UF laser system. The return signals from both the reference and sample arms 106, 110 are then directed by coupler 104 to a detection device 128, which employs a time domain detection technique, a frequency detection technique, or a single point detection technique. In FIG. 1, a frequency domain technique is used with an OCT wavelength of 830 nm and bandwidth of 100 nm.

After exiting the connector 112, the OCT beam 114 is collimated using a lens 116. The size of the collimated OCT beam 114 is determined by the focal length of the lens 116. The size of the beam 114 is dictated by the desired NA at the focus in the eye and the magnification of the beam train leading to the eye 68. Generally, the OCT beam 114 does not require as high an NA as the UF light beam 6 in the focal plane and therefore the OCT beam 114 is smaller in diameter than the UF light beam 6 at the beam combiner 34 location. Following the collimating lens 116 is an aperture 118, which further modifies the resultant NA of the OCT beam 114 at the eye. The diameter of the aperture 118 is chosen to optimize OCT light incident on the target tissue and the strength of the return signal. A polarization control element 120, which may be active or dynamic, is used to compensate for polarization state changes. The polarization state changes may be induced, for example, by individual differences in corneal birefringence. Mirrors 122, 124 are then used to direct the OCT beam 114 towards beam combiners 126, 34. Mirrors 122, 124 can be adjustable for alignment purposes and in particular for overlaying of the OCT beam 114 to the UF light beam 6 subsequent to the beam combiner 34. Similarly, the beam combiner 126 is used to combine the OCT beam 114 with the aim beam 202 as described below.

Once combined with the UF light beam 6 subsequent to beam combiner 34, the OCT beam 114 follows the same path as the UF light beam 6 through the rest of the system. In this way, the OCT beam 114 is indicative of the location of the UF light beam 6. The OCT beam 114 passes through the z-scan 40 and x-y scan 50 devices then the objective lens 58, the contact lens 66, and on into the eye 68. Reflections and scatter off of structures within the eye provide return beams that retrace back through the optical system, into the connector 112, through the coupler 104, and to the OCT detector 128. These return back reflections provide OCT signals that are in turn interpreted by the system as to the location in X, Y, and Z of UF light beam 6 focal location.

The OCT device 100 works on the principle of measuring differences in optical path length between its reference and sample arms. Therefore, passing the OCT beam 114 through the z-adjust device 40 does not extend the z-range of the OCT system 100 because the optical path length does not change as a function of movement of the lens group 42. The OCT system 100 has an inherent z-range that is related to the detection scheme, and in the case of frequency domain detection it is specifically related to the spectrometer and the location of the reference arm 106. In the case of OCT system 100 used in FIG. 1, the z-range is approximately 1-2 mm in an aqueous environment. Extending this range to at least 4 mm involves the adjustment of the path length of the reference arm within OCT system 100. Passing the OCT beam 114 in the sample arm through the z-scan of z-adjust device 40 allows for optimization of the OCT signal strength. This is accomplished by focusing the OCT beam 114 onto the targeted structure while accommodating the extended optical path length by commensurately increasing the path within the reference arm 106 of OCT system 100.

Because of the fundamental differences in the OCT measurement with respect to the UF focus device due to influences such as immersion index, refraction, and aberration, both chromatic and monochromatic, care must be taken in analyzing the OCT signal with respect to the UF beam focal location. A calibration or registration procedure as a function of X, Y, and Z should be conducted in order to match the OCT signal information to the UF focus location and also to the relative to absolute dimensional quantities.

Observation of an aim beam may also be used to assist the user to directing the UF laser focus. Additionally, an aim beam visible to the unaided eye in lieu of the infrared OCT beam and the UF light beam can be helpful with alignment provided the aim beam accurately represents the infrared beam parameters. An aim subsystem 200 is employed in the configuration shown in FIG. 1. The aim beam 202 is generated by an aim beam light source 201, such as a helium-neon laser operating at a wavelength of 633 nm. Alternatively a laser diode in the 630-650 nm range can be used. An advantage of using the helium neon 633 nm beam is its long coherence length, which would enable the use of the aim path as a laser unequal path-length interferometer (LUPI) to measure the optical quality of the beam train, for example.

Once the aim beam light source 201 generates the aim beam 202, the aim beam 202 is collimated using a lens 204. The size of the collimated beam is determined by the focal length of the lens 204. The size of the aim beam 202 is dictated by the desired NA at the focus in the eye and the magnification of the beam train leading to the eye 68. Generally, the aim beam 202 should have close to the same NA as the UF light beam 6 in the focal plane and therefore the aim beam 202 is of similar diameter to the UF light beam 6 at the beam combiner 34. Because the aim beam 202 is meant to stand-in for the UF light beam 6 during system alignment to the target tissue of the eye, much of the aim path mimics the UF path as described previously. The aim beam 202 proceeds through a half-wave plate 206 and a linear polarizer 208. The polarization state of the aim beam 202 can be adjusted so that the desired amount of light passes through the polarizer 208. The half-wave plate 206 and the linear polarizer 208 therefore act as a variable attenuator for the aim beam 202. Additionally, the orientation of polarizer 208 determines the incident polarization state incident upon the beam combiners 126, 34, thereby fixing the polarization state and allowing for optimization of the throughput of the beam combiners 126, 34. Of course, if a semiconductor laser is used as the aim beam light source 200, the drive current can be varied to adjust the optical power.

The aim beam 202 proceeds through a system-controlled shutter 210 and an aperture 212. The system-controlled shutter 210 provides on/off control of the aim beam 202. The aperture 212 sets an outer useful diameter for the aim beam 202 and can be adjusted appropriately. A calibration procedure measuring the output of the aim beam 202 at the eye can be used to set the attenuation of aim beam 202 via control of the polarizer 206.

The aim beam 202 next passes through a beam-conditioning device 214. Beam parameters such as beam diameter, divergence, circularity, and astigmatism can be modified using one or more well known beaming conditioning optical elements. In the case of the aim beam 202 emerging from an optical fiber, the beam-conditioning device 214 can simply include a beam-expanding telescope with two optical elements 216, 218 in order to achieve the intended beam size and collimation. The final factors used to determine the aim beam parameters such as degree of collimation are dictated by matching the UF light beam 6 and the aim beam 202 at the location of the eye 68. Chromatic differences can be taken into account by appropriate adjustments of the beam conditioning device 214. In addition, the optical system 214 is used to image aperture 212 to a desired location such as a conjugate location of the aperture 14.

The aim beam 202 next reflects off of fold mirrors 220, 222, which are preferably adjustable for alignment registration to the UF light beam 6 subsequent to the beam combiner 34. The aim beam 202 is then incident upon the beam combiner 126 where the aim beam 202 is combined with the OCT beam 114. The beam combiner 126 reflects the aim beam 202 and transmits the OCT beam 114, which allows for efficient operation of the beam combining functions at both wavelength ranges. Alternatively, the transmit function and the reflect function of the beam combiner 126 can be reversed and the configuration inverted. Subsequent to the beam combiner 126, the aim beam 202 along with the OCT beam 114 is combined with the UF light beam 6 by the beam combiner 34.

A device for imaging the target tissue on or within the eye 68 is shown schematically in FIG. 1 as an imaging system 71. The imaging system 71 includes a camera 74 and an illumination light source 86 for creating an image of the target tissue. The imaging system 71 gathers images that may be used by the control electronics 300 for providing pattern centering about or within a predefined structure. The illumination light source 86 is generally broadband and incoherent. For example, the light source 86 can include multiple LEDs as shown. The wavelength of the illumination light source 86 is preferably in the range of 700 nm to 750 nm, but can be anything that is accommodated by a beam combiner 56, which combines the viewing light with the beam path for the UF light beam 6 and the aim beam 202 (beam combiner 56 reflects the viewing wavelengths while transmitting the OCT and UF wavelengths). The beam combiner 56 may partially transmit the aim wavelength so that the aim beam 202 can be visible to the viewing camera 74. An optional polarization element 84 in front of the light source 86 can be a linear polarizer, a quarter wave plate, a half-wave plate or any combination, and is used to optimize signal. A false color image as generated by the near infrared wavelength is acceptable.

The illumination light from the light source 86 is directed down towards the eye using the same objective lens 58 and the contact lens 66 as the UF light beam 6 and the aim beam 202. The light reflected and scattered off of various structures in the eye 68 are collected by the same lenses 58, 66 and directed back towards the beam combiner 56. At the beam combiner 56, the return light is directed back into the viewing path via beam combiner 56 and a mirror 82, and on to the viewing camera 74. The viewing camera 74 can be, for example but not limited to, any silicon based detector array of the appropriately sized format. A video lens 76 forms an image onto the camera's detector array while optical elements 80, 78 provide polarization control and wavelength filtering respectively. An aperture or iris 81 provides control of imaging NA and therefore depth of focus and depth of field. A small aperture provides the advantage of large depth of field that aids in the patient docking procedure. Alternatively, the illumination and camera paths can be switched. Furthermore, the aim light source 200 can be made to emit infrared light that would not be directly visible, but could be captured and displayed using the imaging system 71.

Coarse adjust registration is usually needed so that when the contact lens 66 comes into contact with the cornea of the eye 68, the targeted structures are in the capture range of the X, Y scan of the system. Therefore a docking procedure is preferred, which preferably takes in account patient motion as the system approaches the contact condition (i.e. contact between the patient's eye 68 and the contact lens 66). The viewing system 71 is configured so that the depth of focus is large enough such that the patient's eye 68 and other salient features may be seen before the contact lens 66 makes contact with the eye 68.

Preferably, a motion control system 70 is integrated into the overall system 2, and may move the patient, the system 2 or elements thereof, or both, to achieve accurate and reliable contact between the contact lens 66 and the eye 68. Furthermore, a vacuum suction subsystem and flange may be incorporated into the system 2, and used to stabilize the eye 68. Alignment of the eye 68 to the system 2 via the contact lens 66 can be accomplished while monitoring the output of the imaging system 71, and performed manually or automatically by analyzing the images produced by the imaging system 71 electronically by means of the control electronics 300 via the IO 302. Force and/or pressure sensor feedback can also be used to discern contact, as well as to initiate the vacuum subsystem. An alternate patient interface can also be used, such as that described in U.S. patent application Ser. No. 13/225,373, which is incorporated herein by reference.

Figure 2:
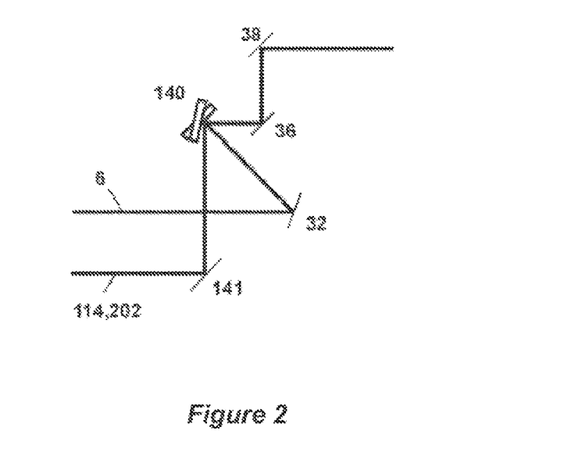
FIG. 2 shows a schematic representation of another embodiment of a system, which utilizing optical multiplexing to deliver treatment and imaging light, that is capable of creating bubbles within the anterior hyaloid vitreous of Berger's space, in accordance with many embodiments.

An alternative beam combining configuration is shown in the alternate embodiment of FIG. 2. For example, the passive beam combiner 34 in FIG. 1 can be replaced with an active combiner 140 as shown in FIG. 2. The active beam combiner 140 can be a moving or dynamically controlled element such as a galvanometric scanning mirror, as shown. The active combiner 140 changes its angular orientation in order to direct either the UF light beam 6 or the combined aim and OCT beams 202,114 towards the scanner 50 and eventually towards the eye 68 one at a time. The advantage of the active combining technique is that it avoids the difficulty of combining beams with similar wavelength ranges or polarization states using a passive beam combiner. This ability is traded off against the ability to have simultaneous beams in time and potentially less accuracy and precision due to positional tolerances of active beam combiner 140.

Figure 3:
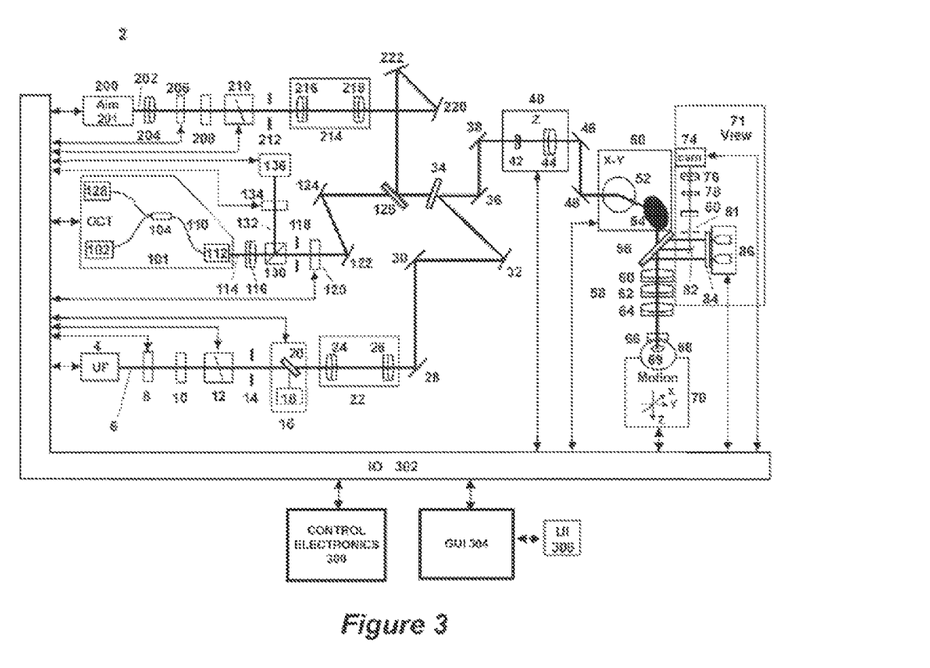
FIG. 3 shows a schematic representation of another embodiment of a system capable of creating bubbles within the anterior hyaloid vitreous of Berger's space utilizing an alternate imaging system configuration, in accordance with many embodiments.

Another alternate embodiment is shown in FIG. 3 and is similar to that of FIG. 1 but utilizes an alternate approach to the OCT 100. In FIG. 3, an OCT 101 is the same as the OCT 100 in FIG. 1, except that the reference arm 106 has been replaced by a reference arm 132. This free-space OCT reference arm 132 is realized by including a beam splitter 130 after the lens 116. The reference beam 132 then proceeds through a polarization controlling element 134 and then onto a reference return module 136. The reference return module 136 contains the appropriate dispersion and path length adjusting and compensating elements and generates an appropriate reference signal for interference with the sample signal. The sample arm of OCT 101 now originates subsequent to the beam splitter 130. Potential advantages of this free space configuration include separate polarization control and maintenance of the reference and sample arms. The fiber based beam splitter 104 of the OCT 101 can also be replaced by a fiber based circulator. Alternately, both the OCT detector 128 and the beam splitter 130 might be moved together as opposed to the reference return module 136.

Figure 4:
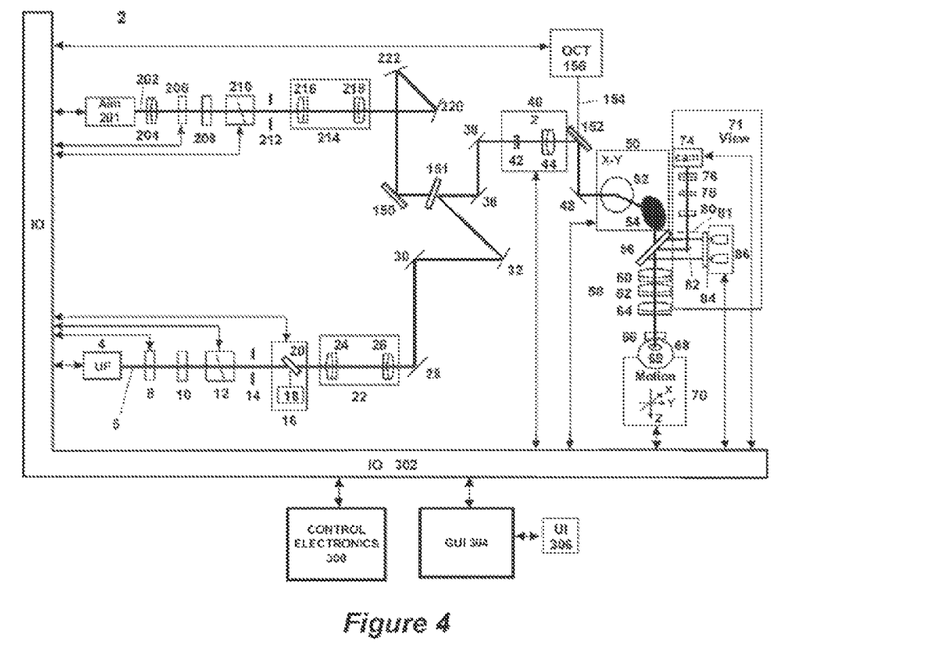
FIG. 4 shows a schematic representation of another embodiment of a system capable of creating bubbles within the anterior hyaloid vitreous of Berger's space utilizing another alternate imaging system configuration, in accordance with many embodiments.

FIG. 4 shows another alternative embodiment for combining the OCT beam 114 and the UF light beam 6. In FIG. 4, an OCT 156 (which can include either of the configurations of OCT 100 or 101) is configured such that an OCT beam 154 output by the OCT 156 is coupled to the UF light beam 6 after the z-scan device 40 using a beam combiner 152. In this way, the OCT beam 154 avoids using the z-scan device 40. This allows the OCT 156 to possibly be folded into the beam more easily and shortening the path length for more stable operation. This OCT configuration is at the expense of an optimized signal return strength as discussed with respect to FIG. 1. There are many possibilities for the configuration of the OCT interferometer, including time and frequency domain approaches, single and dual beam methods, swept source, etc, as described in U.S. Pat. Nos. 5,748,898; 5,748,352; 5,459,570; 6,111,645; and 6,053,613, for example.

The system 2 can be set to locate the surface of the capsule and ensure that the light beam 6 will be focused on the lens capsule at all points of the desired opening. Imaging modalities and techniques described herein, such as for example, Optical Coherence Tomography (OCT), such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the anterior chamber and lens can be performed on the lens using the same laser and/or the same scanner used to produce the patterns for cutting. This scan will provide information about the axial location and shape (and even thickness) of the anterior and posterior lens capsule, the boundaries of the cataract nucleus, as well as the depth of the anterior chamber. This information may then be loaded into the laser 3-D scanning system or used to generate a three dimensional model/representation/image of the anterior chamber and lens of the eye, and used to define the patterns used in the surgical procedure.

The above-described systems can be used to create bubbles within the anterior hyaloid vitreous of Berger's space. By creating a layer of bubbles, Berger's space can be expanded, thereby separating the posterior capsule from the anterior hyaloid surface so that a posterior capsulotomy can be performed on the posterior portion of the lens capsule with reduced risk of compromising the anterior hyaloid surface.

Figure 5:
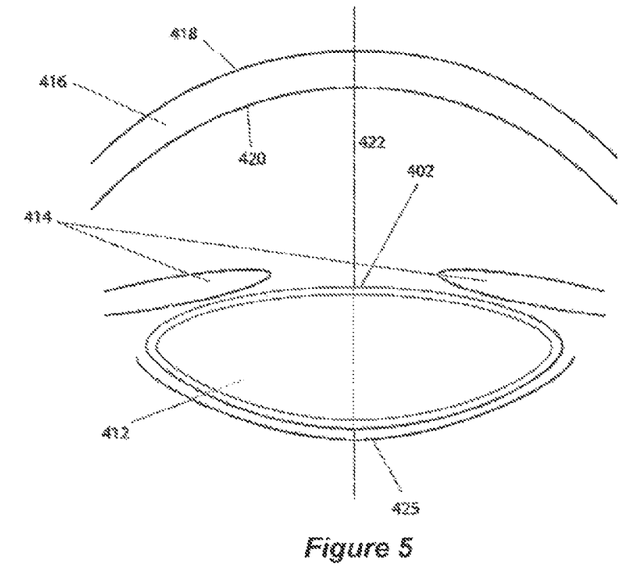
FIG. 5 is a schematic representation of the anterior chamber, lens, and anterior vitreous of the eye, in accordance with many embodiments.

FIG. 5 shows a schematic representation of the anterior chamber, lens, and anterior vitreous of the eye. The eye includes a lens 412, a lens capsule 402, an anterior cornea surface 418, stroma 416, a posterior corneal surface 420, an optical axis 422, an iris 414, and a hyaloid membrane 425. The space between the posterior lens capsular surface and the hyaloid membrane is the capsulo-hyaloidal interspace, also known as Berger's space. This region is filled with an aqueous liquid that is less viscous than the denser, more gelatinous vitreous humor. In accordance with many embodiments, bubbles can be produced within the anterior hyaloid vitreous of Berger's space using, as non-limiting examples, the pulsed laser systems described above.

Figure 6:
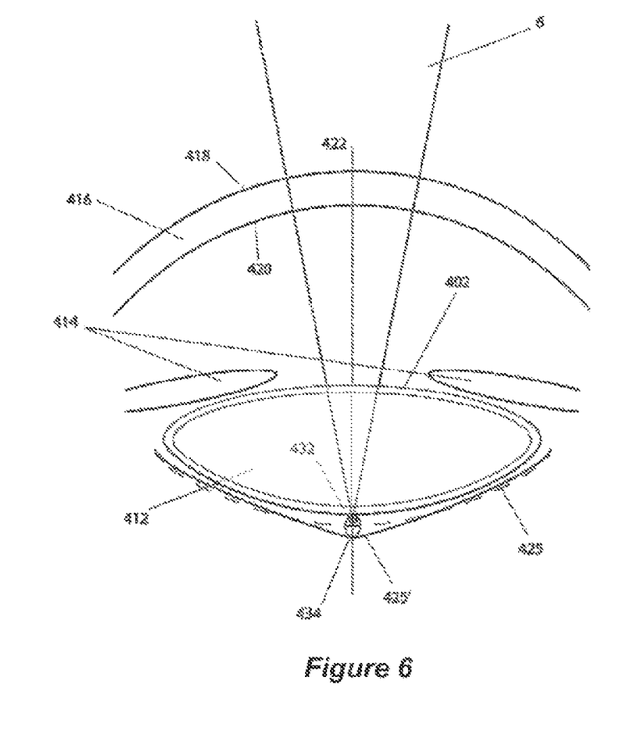
FIG. 6 shows a schematic representation the use of a laser to create a bubble within the anterior hyaloid vitreous of Berger's space, in accordance with many embodiments.

FIG. 6 is a schematic representation of using a laser to form a bubble within the anterior hyaloid vitreous of Berger's space. In this example, the laser beam 6 is focused to a point to cause dielectric breakdown and form plasma 432. The plasma 432 results in a cavitation bubble 434, which can persist for as long as hours, especially if unperturbed. The cavitation bubble 434 causes the hyaloid membrane 425 to be displaced to form the shape as illustrated by a displaced hyaloid membrane 425'. As can be seen in this example, the formation of a bubble in a single location can displace the hyaloid membrane such that it is further away from the posterior portion of the lens capsule 402 in the vicinity of the solitary bubble location, but actually closer to the posterior capsule outside of that vicinity. Once established, a bubble will not provide for efficient further expansion via cavitation due to the lack of available mass within the gas of the bubble as opposed to that of the liquid used to create it. The beam 6, however, can be relocated using scanning systems 40 & 50 to produce bubbles elsewhere and create a broader and/or deeper bubble layer to further increase the volume of Berger's space.

Figure 7:
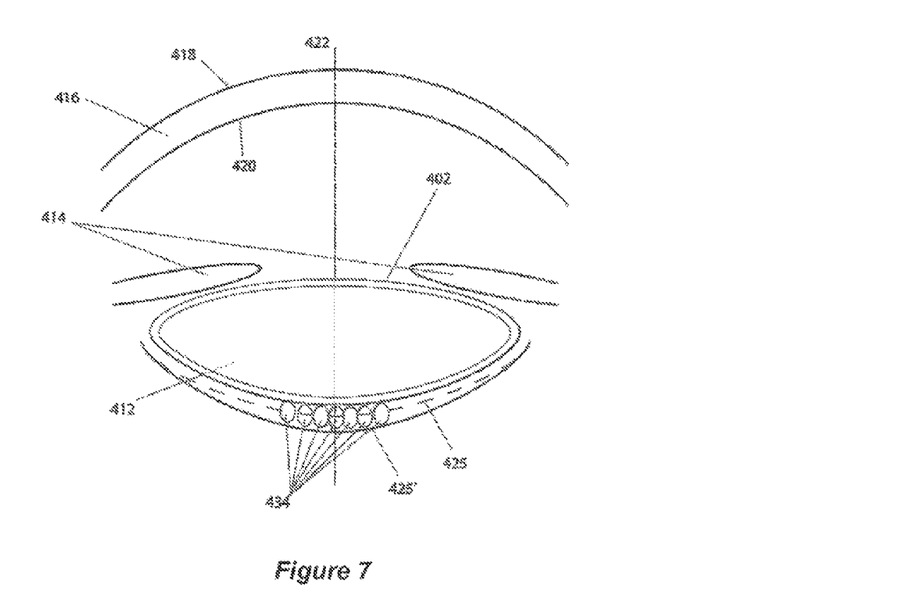
FIG. 7 shows a schematic representation of a layer of bubbles created within the anterior hyaloid vitreous of Berger's space, in accordance with many embodiments.

FIG. 7 shows an example of the results of such a scanning operation. Here, the beam 6 (not longer shown) has been translated using scanners 40 & 50 (also not shown in this rendering) to generate a layer of bubbles 434 that further expand Berger's space.

In many embodiments, the patient can be treated in a supine position so that the gas generated subsequent to the laser creation of plasma and resultant cavitation rises to the posterior capsule. The rising bubbles serve to further separate the posterior capsule from the anterior hyaloid surface.

Figure 8:
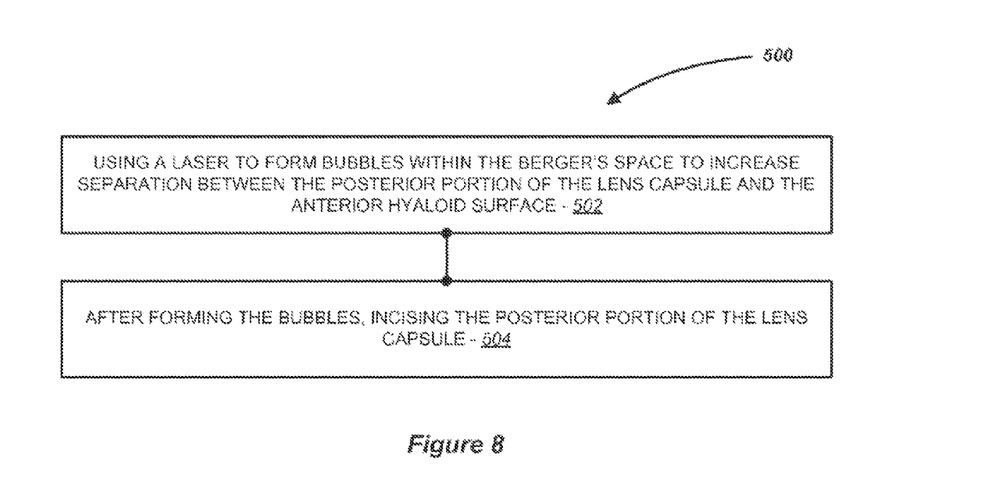
FIG. 8 illustrates a method for using a laser to form a layer of bubbles within the Berger's space of an eye to increase separation between the posterior portion of the lens capsule and the anterior hyaloids surface and, after forming the layer of bubbles, incising the posterior portion of the lens capsule, in accordance with many embodiments.

FIG. 8 illustrates a method 500 for performing laser-assisted surgery on an eye, in accordance with many embodiments. Any suitable system can be used to practice the method 500, including any suitable system described herein and known to a person of ordinary skill in the art.

In act 502, a laser is used to form a plurality of bubbles within the Berger's space of an eye to increase separation between the posterior portion of the lens capsule and the anterior hyaloid surface. In act 504, after forming the plurality of bubbles, the posterior portion of the lens capsule is incised. In many embodiments, the laser is used to perform the incising of the posterior portion of the lens capsule. And in many embodiments, the laser is used to perform a capsulotomy on the posterior portion of the lens capsule.

Any suitable laser can be used to form the bubbles within the Berger's space and/or to incise the posterior portion of the lens capsule. An example of such a suitable system is described U.S. patent application Ser. No. 11/328,970, in the name of Blumenkranz et al., entitled "METHOD AND APPARATUS FOR PATTERNED PLASMA-MEDIATED LASER TREPHENATION OF THE LENS AND CAPSULE IN THREE DIMENSIONAL PHACO-SEGMENTATION", Pub. No. 2006/0195076, the entire disclosure of which is incorporated herein by reference. In many embodiments, the laser is configured to emit a pulsed laser beam into a focal point substantially aligned with the Berger's space. For example, the pulses of the pulsed laser beam can each have a pulse duration between about 10 femtoseconds and about 30 nanoseconds. The pulsed laser beam can have a pulse repetition rate between about 10 Hz and about 1 MHz. The energy of each laser pulse of the pulsed laser beam can be between about 1 micro joule and about 20 micro joules. The pulsed laser beam can have a wavelength between about 500 nanometers and about 1,100 nanometers. When using the laser to form the bubbles, the laser can be irradiated into a focal point substantially aligned with the Berger's space by using an operating numerical aperture of between about 0.005 and about 0.5, a focal spot size diameter between about 1 micron and about 20 microns, and/or with a fluence between about 2 joules per square centimeter and about 200 joules per square centimeter.

Although the above steps show method 500 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 500 may be performed with the circuitry as described herein, for example one or more of the processor or logic circuitry such as the programmable array logic for field programmable gate array. The circuitry may be programmed to provide one or more of the steps of method 500, and the program may comprise program instructions stored on a computer readable memory or programmed steps of the logic circuitry such as the programmable array logic or the field programmable gate array, for example.

Recitation of ranges of values herein are merely intended to serve as a shorthand method of referring individually to each separate value falling within the range, unless otherwise indicated herein, and each separate value is incorporated into the specification as if it were individually recited herein.

All references, including publications, patent applications, and patents, cited herein are hereby incorporated herein by reference in their entirety to the same extent as if each reference were individually and specifically indicated to be incorporated by reference and were set forth in its entirety herein.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A system for performing laser-assisted posterior capsulotomy that minimizes a risk of anterior hyaloid rupture to an eye having a lens capsule with a posterior surface, an anterior hyaloid surface, and a Berger's space between the posterior surface of the lens capsule and the anterior hyaloid surface, the system comprising:

a laser source configured to produce a treatment beam comprising a plurality of laser pulses having a wavelength of 500 to 1100 nm, a pulse duration of 10 fs to 30 ns, a repetition rate of 10 Hz to 1 MHz, and an energy of 1 to 20 µJ;

an integrated optical system comprising an imaging assembly operatively coupled to a treatment laser delivery assembly, wherein the imaging assembly and the treatment laser delivery assembly share at least one common optical element, the integrated optical system being configured to image target tissue structures including the posterior surface of the lens capsule and the anterior hyaloid surface and direct a focal spot of the treatment beam in three-dimensional patterns, wherein the focal spot has a diameter of 1 to 20 microns; and a controller operatively coupled with the laser source and the integrated optical system, the controller including a processor and a computer usable non-transitory medium having a computer readable program code embedded therein, the computer readable program code configured to cause the controller to identify the posterior surface of the lens capsule and the anterior hyaloid surface, and control the laser source and the integrated optical system cooperatively in sequence to:

direct the focal spot of the treatment beam within the Berger's space to form a layer pattern consisting of a plurality of bubbles which extend laterally within the Berger's space in directions transverse to an optical axis of the eye to increase a separation between the posterior surface of the lens capsule and the anterior hyaloid surface;

direct the focal spot of the treatment beam to the posterior surface of the capsule to incise the posterior surface of the lens capsule.

2. The system of claim 1, wherein the the computer readable program code is further configured to cause the controller to control the laser source and the optical system to irradiate the laser beam into a focal point aligned with the Berger's space by using an operating numerical aperture of between 0.005 and 0.5.

* * * * *